United States Patent
Liu et al.

(10) Patent No.: US 11,434,483 B2
(45) Date of Patent: Sep. 6, 2022

(54) METHOD FOR CONSTRUCTING SINGLE CELL SEQUENCING LIBRARY AND USE THEREOF

(71) Applicant: MGI TECH CO., LTD., Guangdong (CN)

(72) Inventors: Longqi Liu, Guangdong (CN); Chuanyu Liu, Guangdong (CN); Liang Wu, Guangdong (CN); Zhouchun Shang, Guangdong (CN); Mengnan Cheng, Guangdong (CN); Yue Yuan, Guangdong (CN); Liqin Xu, Guangdong (CN); Xin Liu, Guangdong (CN); Xun Xu, Guangdong (CN)

(73) Assignee: MGI TECH CO., LTD., Guangdong (CN)

(*) Notice: Subject to any disclaimer, the term of this patent is extended or adjusted under 35 U.S.C. 154(b) by 497 days.

(21) Appl. No.: 16/466,741

(22) PCT Filed: Dec. 7, 2016

(86) PCT No.: PCT/CN2016/108940
§ 371 (c)(1),
(2) Date: Jun. 5, 2019

(87) PCT Pub. No.: WO2018/103025
PCT Pub. Date: Jun. 14, 2018

(65) Prior Publication Data
US 2019/0338279 A1 Nov. 7, 2019

(51) Int. Cl.
*C12N 15/10* (2006.01)
*C40B 50/06* (2006.01)
*C12Q 1/6806* (2018.01)

(52) U.S. Cl.
CPC .......... *C12N 15/1068* (2013.01); *C40B 50/06* (2013.01); *C12Q 1/6806* (2013.01)

(58) Field of Classification Search
None
See application file for complete search history.

(56) References Cited

U.S. PATENT DOCUMENTS

| | | | |
|---|---|---|---|
| 4,243,128 A | 1/1981 | Shirai | |
| 4,574,930 A | 3/1986 | Koitabashi | |
| 6,209,699 B1 | 4/2001 | Hayashi et al. | |

FOREIGN PATENT DOCUMENTS

| | | | |
|---|---|---|---|
| CN | 104561244 A | 4/2015 | |
| CN | 105463089 A | 4/2016 | |
| EP | 1486694 A2 | 12/2004 | |
| KR | 20040034191 A | 4/2004 | |

OTHER PUBLICATIONS

Ackermann et al., "Integration of ATAC-seq and RNA-seq identifies human alpha cell and beta cell signature genes," Mol. Metab. 2016, 5:233-244, published online Jan. 11, 2016. (Year: 2016).*
Buenrostro et al., "ATAC-seq: A Method for Assaying Chromatin Accessibility Genome-Wide," Curr. Protoc. Mol. Biol. 2015, 109: 21.29.1-21.29.9. (Year: 2015).*
Jin et al., "Genome-wide detection of DNase I hypersensitive sites in single cells and FFPE tissue samples," Nature 2015, 528:142-146, with 12 pages of Supplementary Information, published online Nov. 25, 2015. (Year: 2015).*
Hou et al., "Single-cell triple omics sequencing reveals genetic, epigenetic, and transcriptomic heterogeneity in hepatocellular carcinomas," Cell Research 2016, 26:304-319, published online Feb. 23, 2016. (Year: 2016).*
European Search Report and Opinion issued in corresponding European Patent Application No. 18825162.3 dated Mar. 1, 2021.
Office action issued in corresponding patent application No. 16923153. 7-1111 dated Feb. 16, 2021.
Ackermann, et al.: "Intergration of ATAC-seq and RNA-seq identifies human alpha cell and beta cell signature genes", Molecular Metabolism, 5 (2016), pp. 233-244, XP55774574A.
International Search Report issued in PCT/CN2016/108940 dated Sep. 14, 2017.
Liu & Trapnell: "Single-cell transcriptome sequencing: recent advances and remaining challenges", F1000Research 5 (2016), pp. 1-8.
Macaulay, et al.: "Separation and parallel sequencing of the genomes and transcriptomes of single cells using G&T-seq", Nature Protocols, 11(11), (2016), pp. 2081-2103, XP055709425.
Reuter, et al.: "Simul-seq: combined DNA and RNA sequencing for whole-genome and transcriptome profiling", Nature Methods, 13(11), (2016), pp. 953-958, XP055597677.
Angermueller, et al.:"Parallel single-cell sequencing links transcriptional and epigenetic heterogeneity", Nature Mthods 13(3) (2016), pp. 229-234.
Buenrostro, et al."Single-cell chromatin accessibility reveals principles of regulatory variation", Nture (2015), pp. 1-15.
Hou, et al.:"Single-cell triple omics sequencing reveals genetic, epigenetic, and transcriptomic heterogeneity in hepatocellular carcinomas", Cell Research 26 (2016), pp. 304-319.

(Continued)

*Primary Examiner* — Kaijiang Zhang
(74) *Attorney, Agent, or Firm* — Norton Rose Fulbright US LLP; James R. Crawford

(57) ABSTRACT

Provided in the present invention is a method for constructing single cell sequencing libraries, comprising the following steps: a) lysing a single cell to obtain a single cell lysate; b) separating the nucleus and the cytoplasm in the single cell lysate obtained in step a) to obtain a nuclear solution and a total RNA solution; and c) constructing a chromatin DNA library with the nuclear solution obtained in step b) to obtain a chromatin-accessibility sequencing library of the single cell; and constructing a transcriptome library with the total RNA solution obtained in step b) to obtain a transcriptome sequencing library of the single cell.

14 Claims, 2 Drawing Sheets
Specification includes a Sequence Listing.

(56) References Cited

OTHER PUBLICATIONS

Macaulay, et al.: "G&T-seq: parallel sequencing of single-cell genomes and transcriptomes", Nature Methods 12(6) (2015), pp. 519-525.

Tang, et al.: "mRNA-Seq whole-transcriptome analysis of a single cell", Nature Methods 6(5) (2009), pp. 377-384.

* cited by examiner

SEQUENCE LISTING

<160> NUMBER OF SEQ ID NOS: 10

<210> SEQ ID NO 1
<211> LENGTH: 33
<212> TYPE: DNA
<213> ORGANISM: Artificial sequence
<220> FEATURE:
<223> OTHER INFORMATION: synthetic oligonucleotide

<400> SEQUENCE: 1
tcgtcggcag cgtcagatgt gtataagaga cag      33

<210> SEQ ID NO 2
<211> LENGTH: 34
<212> TYPE: DNA
<213> ORGANISM: Artificial sequence
<220> FEATURE:
<223> OTHER INFORMATION: synthetic oligonucleotide

```
<400> SEQUENCE: 2
gtctcgtggg ctcggagatg tgtataagag acag                           34

<210> SEQ ID NO 3
<211> LENGTH: 39
<212> TYPE: DNA
<213> ORGANISM: Artificial sequence
<220> FEATURE:
<223> OTHER INFORMATION: synthetic oligonucleotide

<400> SEQUENCE: 3
gaacgacatg gctacgatcc gactttcgtc ggcagcgtc                      39

<210> SEQ ID NO 4
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 4
tgtgagccaa ggagttgttg tcttc                                     25

<210> SEQ ID NO 5
<211> LENGTH: 15
<212> TYPE: DNA
<213> ORGANISM: Artificial sequence
<220> FEATURE:
<223> OTHER INFORMATION: synthetic oligonucleotide

<400> SEQUENCE: 5
gtctcgtggg ctcgg                                                15

<210> SEQ ID NO 6
<211> LENGTH: 10
<212> TYPE: DNA
<213> ORGANISM: Artificial sequence
<220> FEATURE:
<223> OTHER INFORMATION: synthetic oligonucleotide

<400> SEQUENCE: 6
atttatgaca                                                      10

<210> SEQ ID NO 7
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 7
gaacgacatg gctacgatcc gactt                                     25

<210> SEQ ID NO 8
<211> LENGTH: 26
<212> TYPE: DNA
<213> ORGANISM: Artificial sequence
<220> FEATURE:
<223> OTHER INFORMATION: synthetic oligonucleotide

<400> SEQUENCE: 8
aagcagtggt atcaacgcag agtact                                    26

<210> SEQ ID NO 9
```

```
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 9
aagcagtggt atcaacgcag agtac                                           25

<210> SEQ ID NO 10
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 10
aagcagtggt atcaacgcag agt                                             23
```

METHOD FOR CONSTRUCTING SINGLE CELL SEQUENCING LIBRARY AND USE THEREOF

This patent application is a national phase under 35 U.S.C. § 371 of International Application No. PCT/CN2016/108940 filed Dec. 7, 2016, which is hereby incorporated herein by reference in its entirety for all purposes.

FIELD OF THE INVENTION

The present invention relates to the field of high-throughput sequencing, and in particular to a method for constructing a single-cell sequencing library, a sequencing method based on Single-Cell Multi-Omics Sequencing (SCMOS), and application thereof.

BACKGROUND OF THE INVENTION

Single-cell sequencing technology is one of the most interesting sequencing technologies in recent years. The currently published single-cell sequencing technologies include single-cell DNA and DNA methylation sequencing, single-cell RNA sequencing, and single-cell chromatin accessibility sequencing.

For example, Fuchou Tang et al. (Nature Methods 6, 377-382 (2009)) reported a single-cell RNA sequencing technology, comprising: full lysis of a single cell by a strong lysis buffer, followed by reverse transcription and PCR amplification of the RNA containing a polyadenosine tail, and final library construction and sequencing based on a specific sequencing platform.

For another example, Buenrostro et al. (Nature 523, 486-490 (2015)) reported a single-cell chromatin accessibility sequencing technology, comprising: reduction of a microliter-scale reaction system for 50,000 cells into a nanoliter-scale reaction system for a single cell in proportion by using microfluidic chip technology; insertion of sequencing adaptors in the open chromatin regions by lysing the single cell and treating the single cell chromatin with Tn5 transposase, followed by amplification of the whole open chromatin regions by PCR amplification, and library construction and sequencing.

In addition to the sequencing at single omics level, how to adequately capture multi-omics information in a single cell is currently a challenge. The main problems in single-cell multi-omics sequencing process lie in that the total amount of target substances (such as DNA, RNA, chromatin) in a single cell is very small, and it is very easy to cause losses of the substances during the operations in different dimensions, leading directly to problems such as failure in multi-omics library construction, or low detection sensitivity, serious loss in omics information, high technical noise, high operation error rate, poor repeatability, etc.

At present, an integrated sequencing between single-cell DNA or DNA methylation and single-cell RNA has been achieved. For example, Macaulay et al. (Nature Methods 12, 519-522 (2015)) reported a parallel sequencing of single-cell DNA and RNA, comprising: lysing a cell with a strong lysis buffer, and then capturing the mRNA containing a polyA by using magnetic beads, and after the separation, performing whole genome amplification for the DNA in the remaining liquid for constructing a whole genomic DNA library, and constructing a cDNA library with the RNA. Similarly, on this basis, Angermueller et al. (Nature Methods 13, 229-232 (2016)) developed a method for parallel sequencing of single-cell DNA methylation and RNA, which differed from the former method in that after the DNA and RNA separation, the DNA in the remaining liquid was treated with bisulfite and then a library was constructed with the treated DNA. For another example, Hou et al. (Cell Research 26: 304-319 (2016)) reported another method for parallel sequencing of single-cell DNA methylation and RNA, comprising: firstly, splitting the cell membrane with a weak lysis buffer to release the cytoplasm, with the nucleus being retained, then separating the cytoplasm for RNA library construction, and treating the nucleus with bisulfite for DNA library construction.

However, there is no related report on the integration among other different omics of a single cell, such as a simultaneous sequencing of single-cell RNA and chromatin accessibility.

In the prior art, the assay for transposase-accessible chromatin (ATAC-seq) for a single cell is carried out in a nanoliter-scale reaction system in a microfluidic chip, which is not conducive to the efficient separation of chromatin and RNA, and it is therefore not possible to construct libraries for chromatin accessibility and transcriptome information in a single cell simultaneously.

SUMMARY OF THE INVENTION

In view of the deficiencies existing in the prior art, the present invention provides a method for constructing a single-cell sequencing library, a sequencing method based on Single-Cell Multi-Omics Sequencing (SCMOS), and application thereof. The traditional single-cell chromatin accessibility technology is fully modified and optimized in the present invention, so that not only the single-cell chromatin accessibility library construction can be performed efficiently in a microliter-scale reaction system, but also the chromatin and RNA can be efficiently separated, thereby achieving a simultaneous library construction for chromatin accessibility and RNA, and fully capturing omics information on the chromatin state and gene expression.

The method "Single-Cell Multi-Omics Sequencing" provided in the present invention comprises: segmenting the nucleus and cytoplasm of a single cell, then constructing a chromatin accessibility library with the nucleus, and at the same time, constructing a transcriptome library with the total cytoplasm, for high-throughput sequencing and bioinformatics analysis.

In a first aspect, the present invention provides a method for constructing a single-cell sequencing library that can simultaneously construct chromatin accessibility and transcriptome libraries for a single cell, which comprises the steps of:

a) conducting a first lysis of a single cell to obtain a first single-cell lysate;

b) segmenting the nucleus and cytoplasm in the first single-cell lysate obtained in step a) to obtain a nucleus-containing solution and a total RNA-containing solution;

c) constructing a chromatin DNA library with the nucleus-containing solution obtained in step b) to obtain a chromatin accessibility sequencing library of the single cell; and constructing a transcriptome library with the total RNA-containing solution obtained in step b) to obtain a transcriptome sequencing library of the single cell.

In a preferred specific embodiment, a single lysis system used for the first lysis of the single cell in step a) comprises:

| | |
|---|---|
| Single-cell suspension | ≥0.5 µl; |
| NP-40 | 0.1-0.3%, preferably 0.2%; |
| Tris-HCl, pH 7.5 | 8-12 mM, preferably 10 mM; |
| NaCl | 8-12 mM, preferably 10 mM; |
| RNase inhibitor | 1-2 U/µl, preferably 1.5 U; |
| with the balance being water. | |

It will be understood by one having ordinary skill in the art that in the single lysis system described above, NP-40 has a final concentration of 0.1-0.3%, including any discrete value between 0.1% and 0.3%, such as 0.12%, 0.14%, 0.16%, 0.18%, 0.2%, 0.22%, 0.24%, 0.26%, 0.28%, etc. Likewise, Tris-HCl, pH7.5 has a final concentration of 8-12 mM, including any discrete value between 8 and 12 mM, such as 8.5 mM, 9 mM, 9.5 mM, 10 mM, 10.5 mM, 11 mM, 11.5 mM, etc. NaCl has a final concentration of 8-12 mM, including any discrete value between 8 and 12 mM, such as 8.5 mM, 9 mM, 9.5 mM, 10 mM, 10.5 mM, 11 mM, 11.5 mM, etc. The RNase inhibitor has a final concentration of 1-2 U/µl, including any discrete value between 1 and 2 U/µl, such as 1.1 U/µl, 1.2 U/µl, 1.3 U/µl, 1.4 U/µl, 1.5 U/µl, 1.6 U/µl, 1.7 U/µl, 1.8 U/µl, 1.9 U/µl, etc.

In a preferred specific embodiment, in step c), the chromatin DNA library is constructed by digesting with Tn5 transposase or DNase.

Preferably, the construction of the chromatin DNA library with Tn5 transposase includes the steps of:

c1) cutting the open chromatin regions with Tn5 transposase, comprising fragmenting the chromatin DNA with Tn5 transposase, followed by terminating the fragmentation; and c2) conducting a first amplification of the fragmented chromatin DNA.

In a preferred embodiment, a single fragmentation system used for fragmenting the chromatin DNA in step c1) comprises:

nucleus-containing solution; 5× fragmentation buffer, 0.2 µl/µl a reaction system; TTE Mix V5S, 0.03-0.05 µl/µl, preferably 0.04 µl/µl a reaction system; Tris-HCl, pH 7.5, 8-12 mM, preferably 10 mM; NaCl, 8-12 mM, preferably 10 mM; with the balance being water;

It will be understood by one having ordinary skill in the art that in the single fragmentation system described above, Tris-HCl, pH7.5 has a final concentration of 8-12 mM, including any discrete value between 8 and 12 mM, such as 8.5 mM, 9 mM, 9.5 mM, 10 mM, 10.5 mM, 11 mM, 11.5 mM, etc. Likewise, NaCl has a final concentration of 8-12 mM, including any discrete value between 8 and 12 mM, such as 8.5 mM, 9 mM, 9.5 mM, 10 mM, 10.5 mM, 11 mM, 11.5 mM, etc.

Preferably, after the fragmentation, to the single fragmentation system are added the following components to terminate the fragmentation: EDTA, pH 8.0, 50-70 mM, preferably 60 mM; Tris-HCl, pH8.0, 10-14 mM, preferably 12 mM; with the balance being water.

It will be understood by one having ordinary skill in the art that in the above components for terminating the fragmentation, EDTA, pH 8.0 has a final concentration of 50-70 mM, including any discrete value between 50 and 70 mM, such as 52 mM, 55 mM, 58 mM, 60 mM, 63 mM, 65 mM, 68 mM, etc. Likewise, Tris-HCl, pH 8.0 has a final concentration of 10-14 mM, including any discrete value between 10 and 14 mM, such as 10.5 mM, 11 mM, 11.5 mM, 12 mM, 12.5 mM, 13 mM, 13.5 mM, etc.

In a preferred embodiment, the construction of the chromatin DNA library with Tn5 transposase further includes a second lysis of the product obtained in step c1); further preferably, the second lysis is carried out by using RLT Plus buffer;

In a specific preferred embodiment, the first lysis uses a weak lysis buffer that lyses the cell membrane without affecting the nucleus (i.e., the nucleus is still intact), which facilitates to maintain chromatin integrity in the cell; the second lysis, which is performed after the attack of Tn5 transposase, uses a strong lysis buffer that can completely lyse the nucleus, which facilitates to fully release the chromatin within the nucleus, and thereby maximize the yield of chromatin from a single cell.

Further preferably, a carrier DNA is added to the system in the process of the second lysis; preferably, the carrier DNA is added in an amount of 4-6 ng/µl the system, preferably 5 ng/µl the system. It will be understood by one having ordinary skill in the art that the carrier DNA described above has a final concentration of 4-6 ng/µl the system, including any discrete value between 4 and 6 ng/µl the system, such as 4.2 ng/µl the system, 4.4 ng/µl the system, 4.6 ng/µl the system, 4.8 ng/µl the system, 5.0 ng/µl the system, 5.2 ng/µl the system, 5.4 ng/µl the system, 5.6 ng/µl the system, 5.8 ng/µl the system, etc. Addition of the carrier DNA has the following advantages: since the chromatin DNA content in a single cell is very low (in a pg level), the loss rate due to purification will be high in the subsequent purification process; however, when a large amount of foreign DNA is added before DNA purification, the total amount of DNA is significantly increased, thereby significantly increasing the yield of purification; and moreover, since the carrier DNA is added after the attack of Tn5 transposase and completion of the reaction, there is no adaptor sequence in the carrier DNA, and therefore, there is no interference in the subsequent library construction.

In a preferred embodiment, the construction of the chromatin DNA library with Tn5 transposase further includes the step of: purifying the product from the second lysis prior to the amplification in step c2).

In a preferred embodiment, the construction of the chromatin DNA library with Tn5 transposase further includes a second amplification of the first amplification product obtained in step c2). Since the total amount of DNA in a single cell is small, the inventors present a strategy involving two amplifications. For example, in a specific embodiment, a first 8-cycle amplification is performed by using short specific primers, which can further significantly increase the total amount of DNA. On this basis, a second amplification is performed by using primers containing adaptor sequences, so that the PCR can proceed smoothly by using a large amount of template, thereby ensuring the quality of the library.

In a specific preferred embodiment, a primer pair consisting of the nucleotide sequence 5'-TCGTCGGCAGCGTCAGATGTGTATAAGAGACAG-3' (SEQ ID NO:1) and the nucleotide sequence 5'-GTCTCGTGGGCTCGGAGATGTGTATAAGA-GACAG-3' (SEQ ID NO:2) is used in the first amplification in step c2).

In a specific preferred embodiment, a primer pair consisting of the nucleotide sequence 5'-phos-GAACGACATGGCTACGATCCGACTTTCGTCGGCAG<u>CGTC</u>-3' (the underlined sequence corresponds to SEQ ID NO:3) and the nucleotide sequence 5'-

TGTGAGCCAAGGAGTTGTTGTCTTC (the underlined sequence corresponds to SEQ ID NO:4)-barcode sequence-GTCTCGTGGGCTCGG (the italic sequence corresponds to SEQ ID NO:5)-3' is used in the second amplification.

In a preferred embodiment, a step of determining the number of amplification cycles required for the second amplification by using a real-time fluorescent quantitative PCR is further comprised between the first amplification of step c2) and the second amplification. Specifically, it preferably includes: performing a real-time fluorescent quantitative PCR by using the first amplification product obtained in step c2) as a template and using a primer pair consisting of the nucleotide sequence 5'-TCGTCGGCAGCGTCA-GATGTGTATAAGAGACAG-3' (SEQ ID NO:1) and the nucleotide sequence 5'-GTCTCGTGGGCTCG-GAGATGTGTATAAGAGACAG-3' (SEQ ID NO:2), and finding the number of cycles corresponding to ⅓ of the plateau fluorescence intensity in the resulting linear amplification curve, which is the number of amplification cycles required for the second amplification.

In a preferred embodiment, the construction of the chromatin DNA library with Tn5 transposase further includes the step of: amplifying the constructed chromatin DNA library after completion of the construction of the chromatin DNA library.

In a preferred embodiment of the method for constructing a single-cell sequencing library, the construction of the transcriptome library in step c) includes:

c1') reverse transcribing the total RNA into cDNA, and amplifying the cDNA to obtain a cDNA amplification product;

c2') fragmenting the cDNA amplification product obtained in step c1') with Tn5 transposase, and amplifying the resulting fragmented product to obtain a transcriptome sequencing library of the single cell.

In a preferred embodiment of the method for constructing a single-cell sequencing library, both the constructions of the chromatin DNA library and the transcriptome library in step c) are carried out in a microliter-scale reaction system.

In a second aspect, the present invention provides a method for high-throughput sequencing of a single-cell sequencing library, which comprises the steps of:

subjecting the single-cell sequencing library constructed by the method according to the first aspect to a high-throughput sequencing to obtain information on the chromatin accessibility and on the transcriptome sequence of the single cell, respectively.

In a third aspect, the present invention provides a method for analysis of single-cell multi-omics which comprises:

performing the method according to the second aspect; and performing a bioinformatics analysis on the obtained information on the chromatin accessibility and on the transcriptome sequence of the single cell.

In a fourth aspect, the present invention provides use of the method for constructing a single-cell sequencing library according to the first aspect or the method for analysis of single-cell multi-omics according to the third aspect in at least one selected from the group consisting of tumor target screening, disease surveillance, and pre-implantation genetic diagnosis.

In a fifth aspect, the present invention provides a kit which comprises one or more reagent(s) used in the method according to the first aspect;

preferably, the kit comprises a single-cell lysis reagent used for the first lysis, a chromatin DNA fragmentation reagent, a fragmentation terminating reagent, a lysis reagent used for the second lysis after the chromatin DNA fragmentation, and a carrier DNA;

further preferably, the single cell lysis reagent used for the first lysis comprises:

| | |
|---|---|
| NP-40 | 0.1-0.3%, preferably 0.2%; |
| Tris-HCl, pH 7.5 | 8-12 mM, preferably 10 mM; |
| NaCl | 8-12 mM, preferably 10 mM; |
| RNase inhibitor | 1-2 U/μl, preferably 1.5 U; |
| with the balance being water. | |

It will be understood by one having ordinary skill in the art that in the single-cell lysis reagent used for the first lysis described above, NP-40 has a final concentration of 0.1-0.3%, including any discrete value between 0.1% and 0.3%, such as 0.12%, 0.14%, 0.16%, 0.18%, 0.2%, 0.22%, 0.24%, 0.26%, 0.28%, etc. Likewise, Tris-HCl, pH7.5 has a final concentration of 8-12 mM, including any discrete value between 8 and 12 mM, such as 8.5 mM, 9 mM, 9.5 mM, 10 mM, 10.5 mM, 11 mM, 11.5 mM, etc. Likewise, NaCl has a final concentration of 8-12 mM, including any discrete value between 8 and 12 mM, such as 8.5 mM, 9 mM, 9.5 mM, 10 mM, 10.5 mM, 11 mM, 11.5 mM, etc. The RNase inhibitor has a final concentration of 1-2 U/μl, including any discrete value between 1 and 2 U/μl, such as 1.1 U/μl, 1.2 U/μl, 1.3 U/μl, 1.4 U/μl, 1.5 U/μl, 1.6 U/μl, 1.7 U/μl, 1.8 U/μl, 1.9 U/μl, etc.

Further preferably, the chromatin DNA fragmentation reagent comprises:

| | |
|---|---|
| 5× fragmentation buffer | 1.75×; |
| Tn5 enzyme for fragmentation | 0.05-0.09 U/μl, preferably 0.07 U/μl; |
| Tris-HCl, pH 7.5 | 14-20 mM, preferably 17.5 mM; |
| NaCl | 14-20 mM, preferably 17.5 mM; |
| with the balance being water. | |

It will be understood by one having ordinary skill in the art that in the chromatin DNA fragmentation reagent described above, the Tn5 enzyme for fragmentation has a final concentration of 0.05-0.09 U/μl, including any discrete value between 0.05 and 0.09 U/μl, such as 0.055 U/μl, 0.06 U/μl, 0.065 IRA 0.07 U/μl, 0.075 U/μl, 0.08 IRA 0.085 U/μl, etc. Likewise, Tris-HCl, pH7.5 has a final concentration of 14-20 mM, including any discrete value between 14 and 20 mM, such as 14.5 mM, 15 mM, 15.5 mM, 16 mM, 16.5 mM, 17 mM, 17.5 mM, 18 mM, 18.5 mM, 19 mM, 19.5 mM, etc. Likewise, NaCl has a final concentration of 14-20 mM, including any discrete value between 14 and 20 mM, such as 14.5 mM, 15 mM, 15.5 mM, 16 mM, 16.5 mM, 17 mM, 17.5 mM, 18 mM, 18.5 mM, 19 mM, 19.5 mM, etc.

Further preferably, the fragmentation terminating reagent comprises:

| | |
|---|---|
| EDTA, pH 8.0 | 50-70 mM, preferably 60 mM; |
| Tris-HCl, pH 8.0 | 8-12 mM, preferably 10 mM; |
| with the balance being water. | |

It will be understood by one having ordinary skill in the art that in the fragmentation terminating reagent described above, EDTA, pH 8.0 has a final concentration of 50-70 mM, including any discrete value between 50 and 70 mM, such as 52 mM, 55 mM, 58 mM, 60 mM, 63 mM, 65 mM, 68 mM, etc. Likewise, Tris-HCl, pH 8.0 has a final concentration of 8-12 mM, including any discrete value between 8 and 12 mM, such as 8.5 mM, 9 mM, 9.5 mM, 10 mM, 10.5 mM, 11 mM, 11.5 mM, etc.

Further preferably, the lysis reagent used for the second lysis comprises RLT Plus buffer.

Beneficial Effects

The method for constructing a single-cell sequencing library provided by the present invention can efficiently construct a library for chromatin DNA while construct a library for RNA in the same cell, not only simultaneously obtaining the chromatin accessibility information and the gene expression information of a single cell for the first time, but also reducing the omics information loss during the sequencing process to a very low level. It facilitates the full integration and analysis of the epigenome and transcriptome data of a single cell, the mining of multiple omics information of a single cell, and the establishment of a single-cell gene expression regulatory network. The simultaneous library construction and sequencing method according to the present invention can function as a very useful research tool for the study of single cell gene expression regulation, and has a very good application prospect in basic research such as tumor and development, and in the development of new disease surveillance technology.

In addition, it is worth noting that the existing chromatin accessibility technology is carried out in a nanoliter-scale reaction system in a microfluidic chip, which cannot effectively separate chromatin and RNA; and the microfluidic chip technology is not suitable for automated nucleic acid purification operations. The inventors of the present invention have directly bypassed the defects of being unable to perform physical separation of liquids in the microfluidic chip, and developed a technique for studying chromatin accessibility which is performed in a microliter-scale reaction system. This microliter-scale reaction system can be operated in a single tube (i.e., a single reaction tube), in a single well (i.e., a single reaction well), or in another container that can accommodate microliter quantities of liquid. The method of the present invention greatly optimizes the chromatin accessibility technology, achieves the effective separation of chromatin and RNA, and has achieved notable progress over the prior art by introducing steps of two lysis, addition of a carrier DNA, a second amplification, and the like.

DETAILED DESCRIPTION

Figure 1:
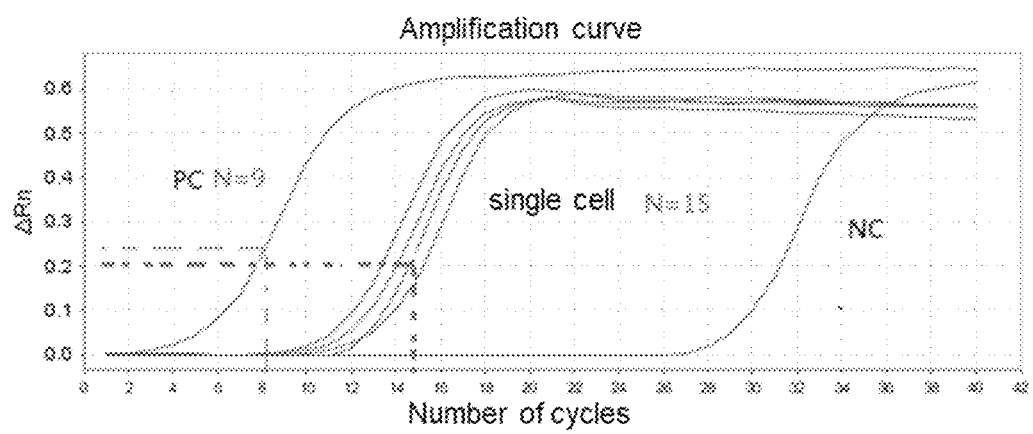
FIG. 1 shows an example of determining the number of amplification cycles required for the second amplification for a chromatin DNA sample by fluorogenic quantitative PCR.

To facilitate an understanding of the present invention, the following examples are enumerated. It should be understood by those skilled in the art that these examples are only intended to facilitate the understanding of the present invention but should not be construed as any limitation of the present invention.

Example Construction of Single-Cell Libraries of 119 ES Cell Line

In this example, a simultaneous construction method of single-cell chromatin accessibility libraries and transcriptome sequencing libraries according to the present invention was carried out by taking H9 ES cell line as an example to prepare single-cell libraries. Specific steps were as follows:

1. Preparation and Lysis of a Single Cell 1.1. Preparation of a Single Cell

The adhered H9 ES cells were digested with Accutase. 1 ml of suspension of the digested cells was taken and centrifuged at 1000 rpm for 5 min, and the cell pellet was resuspended in 1×PBS, repeating the above once. The resuspended cells were diluted to a suitable density, and a single cell (volume less than 0.5 μl) was aspirated by using a glass needle having a diameter less than 200 μm to prepare a cell sample. 100 cells were used as a positive control and PBS was used as a negative control.

1.2. Lysis of a Single Cell

A single-cell lysis system was prepared according to Table 1. 6.5 μl of lysis buffer was added to each single-cell suspension sample (0.5 μl), and mixed by flicking the tube wall gently. The mixture was centrifuged for 3 s, and transferred to a thermal cycler to react at 4° C. for 30 min for cell lysis.

TABLE 1

| Reagent | Volume (μl) |
| --- | --- |
| Single-cell suspension | 0.5 |
| 10% NP-40 (Sigma, Cat. No. I8896) | 0.07 |
| 1M Tris-HCl (pH 7.5) (Invitrogen) | 0.07 |
| 1M NaCl (Sigma) | 0.07 |
| RNAse inhibitor (40 U/μl) (Takara, 2313A) | 0.25 |
| Nuclease-free water (Ambion AM9932) | 6.04 |
| Total | 7 |

2. Cell Nucleus/RNA Separation 2.1 After the lysis, the tube was vortexed for 1 min, and centrifuged at 4° C. at 1000 g for 5 min;

2.2 4 μl of supernatant was carefully pipetted into a new PCR tube. 3 μl of the remaining liquid was a nucleus-containing solution. The RNA was in the supernatant.

3. Nucleus and chromatin DNA library construction with Tn5

3.1 Cutting the open chromatin regions with Tn5

3.1.1 5× Tagament Buffer L was thawed at room temperature and mixed by turning upside down for use.

3.1.2. A Tn5-based fragmentation reaction system was prepared according to Table 2, mixed by flicking the tube wall gently, and centrifuged for 3 s.

TABLE 2

| Reagent | Volume (μl) |
| --- | --- |
| DNA solution (the nucleus-containing solution obtained in step 2.2) | 3 |
| 5x Tagament buffer L (5x fragmentation buffer, BGE005B01) | 1.4 |
| TTEMix V5S (Tn5 enzyme V5S, BGE005S, for fragmentation) | 0.3 |

TABLE 2-continued

| Reagent | Volume (μl) |
| --- | --- |
| 1M Tris, pH 7.5 (Invitrogen) | 0.07 |
| 1M NaCl (Sigma) | 0.07 |
| Nuclease-free water (Ambion) | 2.16 |
| Total | 7 |

3.1.3 The tube was transferred to a thermal cycler to react at 37° C. for 30 min.

3.1.4 Reagents for terminating the Tn5-based fragmentation were prepared according to Table 3, and mixed uniformly. 3.5 μl of the reagents for terminating the fragmentation were added to the fragmented product obtained as above, mixed by flicking the tube wall gently, and centrifuged for 3 s.

TABLE 3

| Reagent | Volume (μl) |
| --- | --- |
| 0.1M EDTA, pH 8.0 (Ambion) | 2.1 |
| 0.1M Tris, pH 8.0 (Ambion) | 0.42 |
| Nuclease-free water (Ambion) | 0.98 |
| Total | 3.5 |

3.1.5 The tube was transferred to a thermal cycler to react at 50° C. for 30 min.

3.2 Second lysis and addition of a carrier DNA 3.2.1 Reagents for the second lysis were prepared according to Table 4 and mixed uniformly. To the product obtained in step 3.1.5, 6 μl of the reagents were added (with a total volume of 16.5 μl), centrifuged for 3 s, and left at room temperature for 15 min.

TABLE 4

| Reagent | Volume (μl) |
| --- | --- |
| RLT Plus buffer (Qiagen, Cat. No. 1053393) | 3 |
| 10 ng/μl of the carrier DNA | 3 |
| Total | 6 |

In Table 4, the carrier DNA was a foreign DNA with a fragment size of between 1 kb and 10 kb and being heterologous to the genome of the cell of interest. It may be linear or circular. For example, a DNA fragment derived from bacteria satisfying the requirements, or a conventional plasmid cloning carrier can be used as a carrier DNA.

3.2.2 Sterilized ultrapure water was added to 40 μl, mixed by flicking the tube wall gently, and centrifuged for 3 s.

3.3 DNA purification

In order to avoid interference from other substances in the subsequent PCR reaction system, DNA purification was carried out in this step. Specifically, purification was carried out by using Agencourt AMPure XP magnetic beads (1.8×) and finally the DNA was dissolved in 9 μl of sterilized ultrapure water.

3.4 First DNA amplification 3.4.1 Reagents for the first amplification were prepared according to Table 5 and mixed uniformly. 11 μl of the reagents for the first amplification were added to the purified product obtained in step 3.3, mixed by flicking the tube wall gently, and centrifuged for 3 s.

TABLE 5

| Reagent | Volume (μl) |
| --- | --- |
| High-Fidelity 2X PCR Master Mix (NEB, Cat. No. M0541L) | 10 |
| Primer B (20 μM) | 0.5 |
| Primer C (20 μM) | 0.5 |
| Total | 11 |

Wherein primer B had the sequence (as shown in SEQ ID NO: 1) of:

5'-TCGTCGGCAGCGTCAGATGTGTATAAGAGACAG-3';

Primer C had the sequence (as shown in SEQ ID NO: 2) of:

5'-GTCTCGTGGGCTCGGAGATGTGTATAAGAGACAG-3'

3.4.2 The tube was transferred to a thermal cycler to undergo the following procedure, 72° C. 5 min; 98° C. 1 min; 98° C. 15 s, 63° C. 30 s, 72° C. 1 min, 8 cycles.

3.4.3 Purification was carried out by using Agencourt AMPure XP magnetic beads (1.8×), and finally the DNA was dissolved in 20 μl of sterilized ultrapure water.

3.5 Determination of the cycle numbers of PCR required for the second amplification by using real-time fluorescent quantitative PCR 3.5.1 4 μl of the purified product obtained in step 3.4.3 was transferred into a new PCR tube.

3.5.2 Reagents for the amplification were prepared according to Table 6 and mixed uniformly. 16 μl of the reagents for the amplification were added to the PCR tube containing the purified product obtained in step 3.5.1, mixed by flicking the tube wall gently, and centrifuged for 3 s.

TABLE 6

| Reagent | Volume (μl) |
| --- | --- |
| 2x SYBR ® Premix Ex Taq ™ II (Takara, Cat. No. RR820W) | 10 |
| Primer B (20 μM) | 0.5 |
| Primer C (20 μM) | 0.5 |
| Fluorescent dye ROX (Takara, Cat. No. RR820W) | 0.08 |
| Nuclease-free water (Ambion) | 4.92 |
| Total | 16 |

3.5.3 The tube was transferred to a fluorescence quantitative PCR instrument to undergo the following procedure, 72° C. 5 min; 98° C. 30 s; 98° C. 10 s, 63° C. 30 s, 72° C. 1 min, 40 cycles.

3.5.4 The number of cycles corresponding to ⅓ of the plateau fluorescence intensity in the linear amplification Rn/Cycle curve was the number N of cycles required for the second amplification, as shown in FIG. 1.

3.6 The second DNA amplification 3.6.1 Reagents for the second amplification were prepared according to Table 7 and mixed uniformly. 17.1 µl of the reagents for the second amplification were added to the purified product obtained in step 3.4.3, and 0.7 µl of barcode primer N7 was further added, mixed by flicking the tube wall gently, and centrifuged for 3 s.

TABLE 7

| Reagent | Volume (µl) |
|---|---|
| High-Fidelity 2X PCR Master Mix (NEB, Cat. No. M0541L) | 16.4 |
| N5 (25 µM) | 0.7 |
| Total | 17.1 |

Wherein N5 primer had the sequence of:

5'-phos-GAACGACATGGCTACGATCCGACTTTCGTCGGCAGCGTC-3' (i.e. SEQ ID NO: 3);

N7 primer had the sequence of:

5'-TGTGAGCCAAGGAGTTGTTGTCTTC(i.e. SEQ ID NO: 4)-barcode sequence-GTCTCGTGGGCTCGG(i.e. SEQ ID NO: 5)-3'.

Specifically, the barcode sequence may be 5'-ATTTATGACA-3' (i.e. SEQ ID NO: 6).

3.6.2 The tube was transferred to a thermal cycler to undergo the following procedure, 72° C. 5 min; 98° C. 1 min; 98° C. 15 s, 63° C. 30 s, 72° C. 1 min, N cycles (N was the number of cycles as determined in 3.5.4).

3.6.3 Purification was carried out by using Agencourt AMPure XP magnetic beads (1×), and finally the DNA was dissolved in 20 µl of sterilized ultrapure water.

Figure 2:
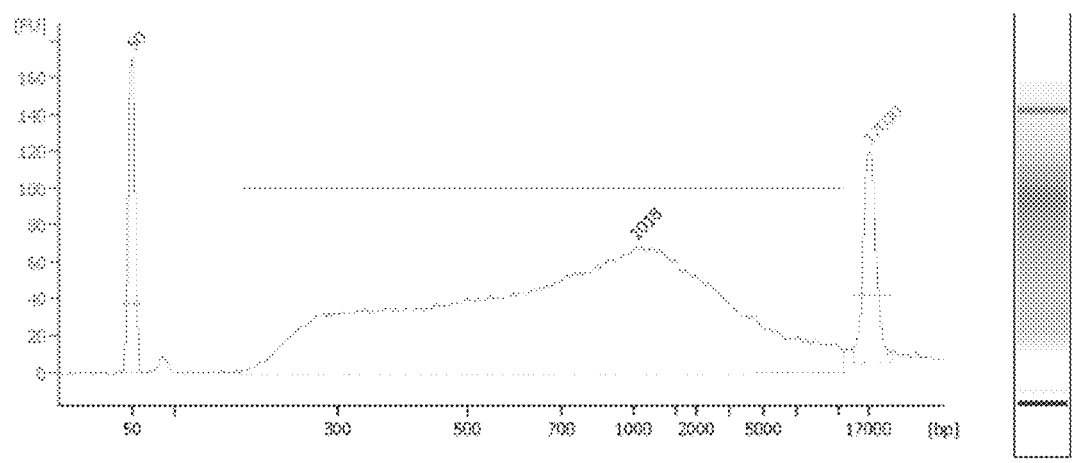
FIG. 2 shows an example of the amplification result of the fragmentation product of a chromatin DNA sample.

3.7 Product concentrations were determined by Qubit, and library construction results were tested with Agilent 2100. The desired library should be distributed above 100 bp, as shown in FIG. 2.

Optionally, the constructed chromatin DNA library can be amplified with the specific amplification system as shown in Table 8:

TABLE 8

| Reagent | Volume (µl) |
|---|---|
| DNA solution (the solution obtained in 3.6.3) | X (20 ng) |
| 2x KAPA HiFi HotStart ReadyMix (KAPA BIOSYSTEMS, Cat. No. KK2602) | 25 |
| Primer 1 (20 µM) | 1.5 |
| Primer 2 (20 µM) | 1.5 |
| Nuclease-free water (Ambion) | 22-X |
| Total | 50 |

Wherein primer 1 had the sequence of:

5'-phos-GAACGACATGGCTACGATCCGACTT-3' (the underlined sequence was SEQ ID NO: 7);

Primer 2 had the sequence of:

5'-TGTGAGCCAAGGAGTTGTTGTCTTC-3' (i.e. SEQ ID NO: 4).

3.8 Further, pre-processing and sequencing were performed based on a specific sequencing platform.

4. Preparation of a cDNA sample from the total RNA, fragmentation of the cDNA sample, and library construction.

4.1 Reverse transcription of the total RNA to cDNA

Names and Sequences of the Reference Primers:

Oligo-dT:

5'-AAGCAGTGGTATCAACGCAGAGTACT30VN-3' (the underlined sequence was SEQ ID NO: 8);

Template-Switching Oligo (LNA):

5'-AAGCAGTGGTATCAACGCAGAGTACrGrG+G-3' (wherein the underlined sequence was SEQ ID NO: 9, the rG was an RNA base, and the +G was a locked nucleic acid (LNA) modification).

4.1.1 1 µl of oligo-dT (10 µM) and 1 µl of dNTP (10 mM) (ENZYMATICS) were added to the pipetted RNA supernatant in step 2.2, mixed by flicking the tube wall gently, and centrifuged for 3 s. The tube was transferred to a thermal cycler to react at 72° C. for 3 min. After the reaction, materials were centrifuged to the bottom of the tube, and placed on ice for use.

4.1.2 A reverse transcription system was prepared according to Table 9, mixed by flicking the tube wall gently, and centrifuged for 3 s.

TABLE 9

| Reagent | Volume (µl) |
|---|---|
| RNA solution (the solution obtained in step 4.1.1) | 6 |
| SuperScript II reverse transcriptase 200 U/µl (Invitrogen, Cat. No. 18064) | 0.75 |
| RNAse inhibitor 40 U/µl (Takara) | 0.375 |
| 5xSuperscript II First-Strand Buffer (Invitrogen, Cat. No. 18064) | 3 |
| 100 mM DTT (Invitrogen) | 0.75 |
| 5M Betaine (SIGMA, Cat. No. B0300-1VL) | 3 |
| 0.2M MgCl$_2$ (MILLIPORE) | 0.45 |
| 100 µM Template-Switching Oligo (LNA) (EXIQON,Cat. No. 500100) | 0.15 |
| Nuclease-free water (Ambion) | 0.525 |
| Total | 15 |

4.1.3 The tube was transferred to a thermal cycler to undergo the following procedure, 42° C. 90 min; 50° C. 2 min, 42° C. 2 min, 10 cycles; 72° C. 5 min.

4.2 cDNA amplification

Name and Sequence of the Reference Primer

IS primer:

(SEQ ID NO: 10)
5'-AAGCAGTGGTATCAACGCAGAGT-3'.

4.2.1 A cDNA amplification system was prepared according to Table 10, mixed by flicking the tube wall gently, and centrifuged for 3 s.

TABLE 10

| Reagent | Volume (µl) |
|---|---|
| cDNA solution (the product obtained in step 4.1.3) | 15 |
| 2x KAPA HiFi HotStart Ready Mix (KAPA BIOSYSTEMS, Cat. No. KK2602) | 14.7 |
| 10 µM IS Primer | 0.3 |
| Total | 30 |

4.2.2 The tube was transferred to a thermal cycler to undergo the following procedure, 98° C. 3 min; 98° C. 20 s, 67° C. 20 s, 72° C. 6 min, 20 cycles; 72° C. 5 min.

4.2.3 cDNA Purification

Purification was carried out by using Agencourt AMPure XP magnetic beads.

Figure 3:
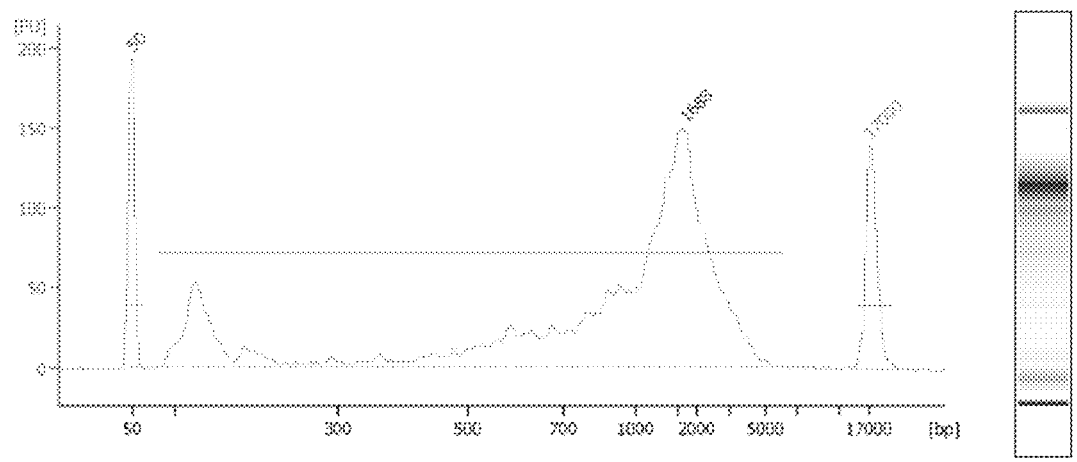
FIG. 3 shows an example of the amplification result of a cDNA sample.

4.2.4 The cDNA amplification results were detected by Agilent 2100, as shown in FIG. 3.

4.3 cDNA library construction with Tn5

4.3.1 cDNA fragmentation 4.3.1.1 5× Tagament Buffer L was thawed at room temperature and mixed by turning upside down for use.

4.3.1.2 A Tn5 fragmentation system was prepared according to Table 11. The components were mixed thoroughly by gently pipetting 20 times with a pipette, and centrifuged for 3 s.

TABLE 11

| Reagent | Volume (μl) |
|---|---|
| 1 ng/μl cDNA (the purified product obtained in step 4.2.3) | 2 |
| 5× Tagment Buffer L (5× fragmentation buffer, BGE005B01) | 2 |
| Tagment Enzyme Advanced Mix V5S (Tn5 enzyme V5S, BGE005S, for fragmentation) | 0.8 |
| Nuclease-free water (Ambion) | 5.2 |
| Total | 10 |

4.3.1.3 The PCR tube was incubated in a thermal cycler at 55° C. for 10 min, and was taken out when the sample temperature dropped to 4° C.

4.3.1.4 2.5 μl of 5×NT Solution was added to the product obtained in step 4.3.1.3, mixed thoroughly by gently pipetting 20 times with a pipette, and left at room temperature for 5 min.

4.3.2 Amplification of the fragmented cDNA product

Names and sequences of the reference primers:

Pimer 1, primer 2, N5 primer, and N7 primer, with the sequences as described above, were used for the amplification in this step.

4.3.2.1 A reaction system for amplifying the product of the cDNA fragmentation was prepared according to Table 12, mixed by flicking the tube wall gently, and centrifuged for 3 s.

TABLE 12

| Reagent | Volume (μl) |
|---|---|
| cDNA solution (the product obtained in step 4.3.1.4) | 12.5 |
| Primer 1 (10 μM) | 1 |
| Primer 2 (10 μM) | 1 |
| Primer N5 (0.5 μM) | 1 |
| Primer N7 (0.5 μM) | 1 |
| 2× KAPA HiFi HotStart Ready Mix | 25 |
| Nuclease-free water (Ambion) | 8.5 |
| Total | 50 |

4.3.2.2 The tube was transferred to a thermal cycler to undergo the following procedure, 72° C. 5 min; 95° C. 3 min; 98° C. 20 s, 60° C. 15 s, 72° C. 30 s, 16 cycles; 72° C. 5 min.

4.3.2.3 The PCR product was selectively purified by using Agencourt AMPure XP magnetic beads.

Figure 4:
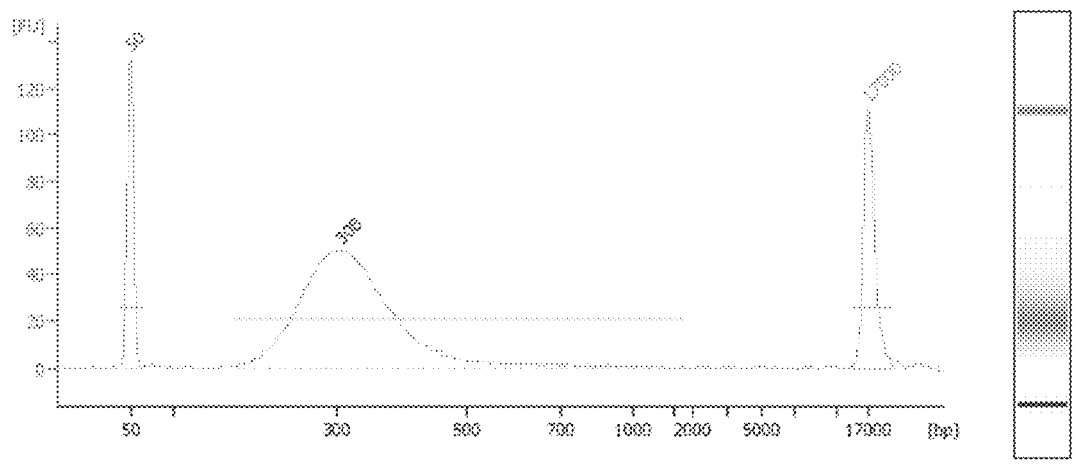
FIG. 4 shows an example of the amplification result of the fragmentation product of a cDNA sample.

4.3.2.4 Product concentrations were determined by Qubit, and library construction results were tested with Agilent 2100. The desired library had a main peak of between 150 and 350 bp, as shown in FIG. 4.

5. High-throughput sequencing and data analysis

The libraries constructed as above can be sequenced by using a next-generation sequencing platform which is currently mainstream (e.g., BGISEQ-500, Hiseq2000, Hiseq4000, etc.). The sequencing platform used in this example was BGISEQ-500. The post-sequencing analysis included separate filtering of single-cell accessibility and transcriptome data, data alignment, and downstream mining and analysis of personalized data.

The applicant declares that methods of the present invention and use thereof have been demonstrated through the above embodiments, and however, the present invention is not limited thereto. It should be apparent to those skilled in the art that, for any improvement of the present invention, the equivalent replacement and addition of the parameters or steps involved in the methods of the present invention, and the selection of specific modes, etc., will all fall within the protection scope and the disclosure scope of the present invention.

The invention claimed is:

1. A method for constructing single-cell sequencing libraries, comprising the steps of:
   a) conducting a first lysis of a single cell to obtain a first single-cell lysate;
   b) segmenting the nucleus and the cytoplasm in the first single-cell lysate obtained in step a) to obtain a nucleus-containing solution and a total RNA-containing solution;
   c) constructing a chromatin DNA library with the nucleus-containing solution obtained in step b) to obtain a chromatin accessibility sequencing library of the single cell; and constructing a transcriptome library with the total RNA-containing solution obtained in step b) to obtain a transcriptome sequencing library of the single cell,
   wherein, in step c), the chromatin DNA library is constructed by digesting with Tn5 transposase, wherein the construction of the chromatin DNA library by using Tn5 transposase includes the steps of:
   c1) cutting the open chromatin regions with Tn5 transposase, comprising fragmenting the chromatin DNA with Tn5 transposase, followed by terminating the fragmentation; and
   c2) performing a second lysis of the product obtained in step c1); and then conducting a first amplification of the fragmented chromatin DNA.

2. The method according to claim 1, wherein the second lysis is carried out by using RLT Plus buffer.

3. The method according to claim 2, wherein the construction of the chromatin DNA library by using Tn5 transposase further includes:
   a second amplification of the first amplification product obtained in step c2).

4. The method according to claim 3, wherein a primer pair consisting of the nucleotide sequence 5'-TCGTCGGCAGCGTCAGATGTGTATAAGAGACAG (SEQ ID NO: 1)-3' and the nucleotide sequence 5'-GTCTCGTGGGCTCGGAGATGTGTATAAGA-GACAG(SEQ ID NO: 2)-3' is used in the first amplification in step c2);
   and a primer pair consisting of the nucleotide sequence 5'-phos-GAACGACATGGCTAC-GATCCGACTTTCGTCGGCAGCGTC(SEQ ID NO: 3)-3' and the nucleotide sequence 5'-TGTGAGC-CAAGGAGTTGTTGTCTTC(SEQ ID NO: 4)-barcode sequence-GTCTCGTGGGCTCGG(SEQ ID NO: 5)-3' is used in the second amplification.

5. The method according to claim 3, wherein a step of determining the number of amplification cycles required for the second amplification by using a real-time fluorescent quantitative PCR is further comprised between the first amplification of step c2) and the second amplification.

6. The method according to claim 5, wherein the step of determining the number of amplification cycles required for the second amplification comprises: performing a real-time fluorescent quantitative PCR by using the first amplification product obtained in step c2) as a template and using a primer pair consisting of the nucleotide sequence 5'-TCGTCGGCAGCGTCAGATGTGTATAAGAGACAG (SEQ ID NO: 1)-3' and the nucleotide sequence 5'-GTCTCGTGGGCTCGGAGATGTGTATAAGA-GACAG(SEQ ID NO: 2)-3', and finding the number of cycles corresponding to ⅓ of the plateau fluorescence intensity in the resulting linear amplification curve, which is the number of amplification cycles required for the second amplification.

7. The method according to claim 3, wherein the constructed chromatin DNA library is amplified after completion of the construction of the chromatin DNA library.

8. The method according to claim 2, wherein a carrier DNA is added to the system in the process of the second lysis.

9. The method according to claim 8, wherein the carrier DNA is added in an amount of 4-6 ng per µl of the the system volume.

10. The method according to claim 1, wherein a single fragmentation system used for fragmenting the chromatin DNA in step c1) comprises:
    the nucleus-containing solution; 5× fragmentation buffer, 0.2 µl a per µl of the reaction system volume; TTE Mix V5S, 0.03-0.05 µl per µl of the reaction system volume; Tris-HCl, pH 7.5, 8-12 mM; NaCl, 8-12 mM; with the balance being water.

11. The method according to claim 1, wherein the construction of the transcriptome library includes:
    c1') reverse transcribing the total RNA into cDNA, and amplifying the cDNA to obtain a cDNA amplification product;

c2') fragmenting the cDNA amplification product obtained in step c1') with Tn5 transposase, and amplifying the resulting fragmented product to obtain a transcriptome sequencing library of the single cell.

12. The method according to claim 1, wherein both the constructions of the chromatin DNA library and the transcriptome library in step c) are carried out in a microliter-scale reaction system.

13. The method according to claim 1, wherein a single first lysis system used for the first lysis of the single cell in step a) comprises:

| | |
|---|---|
| Single-cell suspension | ≥0.5 μl; |
| NP-40 | 0.1-0.3% |
| Tris-HCl, pH 7.5 | 8-12 mM; |
| NaCl | 8-12 mM; |
| RNase inhibitor | 1-2 U/μl; |
| with the balance being water. | |

14. A method for analysis of single-cell multi-omics, comprising:
   subjecting the chromatin accessibility sequencing library and the transcriptome sequencing library constructed by the method according to claim 1 to a high-throughput sequencing to obtain information on the chromatin accessibility and on the transcriptome sequence of the single cell, respectively; and
   performing a bioinformatics analysis on the obtained information on the chromatin accessibility and on the transcriptome sequence of the single cell.

* * * * *